(12) United States Patent
Binns et al.

(10) Patent No.: US 7,555,439 B1
(45) Date of Patent: Jun. 30, 2009

(54) COMPUTERIZED MEDICAL UNDERWRITING OF GROUP LIFE INSURANCE USING MEDICAL CLAIMS DATA

(75) Inventors: Gregory S. Binns, Lake Forest, IL (US); Mark Stuart Blumberg, Oakland, CA (US)

(73) Assignee: TruRisk, LLC, Lake Forest, IL (US)

( * ) Notice: Subject to any disclaimer, the term of this patent is extended or adjusted under 35 U.S.C. 154(b) by 0 days.

(21) Appl. No.: 11/491,325

(22) Filed: Jul. 21, 2006

Related U.S. Application Data (60) Provisional application No. 60/701,311, filed on Jul. 21, 2005.

(51) Int. Cl.
*G06Q 10/00* (2006.01)
(52) U.S. Cl. .................. 705/4; 705/2; 705/3; 600/300; 600/301
(58) Field of Classification Search .................. 705/2–4, 705/35
See application file for complete search history.

(56) References Cited

U.S. PATENT DOCUMENTS

| | | | |
|---|---|---|---|
| 4,667,292 A | 5/1987 | Mohlenbrock et al. | |
| 4,750,121 A | 6/1988 | Halley et al. | |
| 4,975,840 A * | 12/1990 | DeTore et al. .................. | 705/4 |
| 5,018,067 A | 5/1991 | Mohlenbrock et al. | |
| 5,544,044 A | 8/1996 | Leatherman | |
| 5,557,514 A | 9/1996 | Seare et al. | |
| 5,613,072 A | 3/1997 | Hammond et al. | |
| 5,652,842 A | 7/1997 | Siegrist, Jr. et al. | |
| 5,712,984 A | 1/1998 | Hammond et al. | |
| 5,724,379 A | 3/1998 | Perkins et al. | |
| 5,754,980 A | 5/1998 | Anderson et al. | |
| 5,809,478 A | 9/1998 | Greco et al. | |
| 5,835,897 A | 11/1998 | Dang | |
| 5,873,066 A | 2/1999 | Underwood et al. | |
| 5,893,072 A | 4/1999 | Zizzamia | |

(Continued)

FOREIGN PATENT DOCUMENTS

JP 2002-049745 2/2002

(Continued)

OTHER PUBLICATIONS

English translation of abstract of JP 2002049745A.

(Continued)

*Primary Examiner*—Vivek D. Koppikar
(74) *Attorney, Agent, or Firm*—Husch Blackwell Sanders Welsh & Katz (57) ABSTRACT

A method of underwriting group life insurance for a policy period includes collecting medical claims data for the group to be underwritten, where each medical claim being related to a particular employee of the group. Morbidity categories are provided that categorize the medical claims in the medical claims data. A conditional probability model is developed and applied to the morbidity categories for each employee in the group using his medical claims, thereby calculating the expected conditional probability for each employee dying during the policy period. For each employee, an estimate of the expected life claim cost is estimated using an index of the life coverage to salary. Combining the expected conditional probability for each employee dying during the policy period with the estimate of the expected claim cost of death gives an estimate of the group's total life exposure.

6 Claims, 5 Drawing Sheets

U.S. PATENT DOCUMENTS

| | | | |
|---|---|---|---|
| 5,918,208 A | | 6/1999 | Javitt |
| 5,926,800 A | * | 7/1999 | Baronowski et al. .......... 705/35 |
| 5,970,464 A | | 10/1999 | Apte et al. |
| 5,976,082 A | | 11/1999 | Wong et al. |
| 6,061,657 A | | 5/2000 | Whiting-O'Keefe |
| 6,078,890 A | | 6/2000 | Mangin et al. |
| 6,223,164 B1 | | 4/2001 | Seare et al. |
| 6,611,815 B1 | | 8/2003 | Lewis et al. |
| 6,647,374 B2 | | 11/2003 | Kansal |
| 7,249,040 B1 | * | 7/2007 | Binns et al. .................... 705/4 |
| 2002/0188480 A1 | | 12/2002 | Liebeskind et al. |
| 2003/0093304 A1 | * | 5/2003 | Keller et al. ................... 705/4 |
| 2003/0187697 A1 | | 10/2003 | Bonissone et al. |
| 2003/0200121 A1 | | 10/2003 | Santoloci |
| 2003/0200123 A1 | | 10/2003 | Burge et al. |
| 2004/0236611 A1 | * | 11/2004 | Bonissone et al. ............. 705/4 |
| 2006/0015373 A1 | | 1/2006 | Cuypers |

FOREIGN PATENT DOCUMENTS

| | | | |
|---|---|---|---|
| JP | 2002-49745 | * | 2/2002 |

OTHER PUBLICATIONS

Ash et al., "Using Claims Data to Examine Mortality Trends Following Hospitalization for Heart Attack in Medicare," Health Services Research, (38) 5: 1253-1262 Oct. 2003.

"Harvard Pilgrim/DxCG"; Insurance & Technology, vol. 27, No. 10, p. 10, Sep. 2002.

Steven Boyce, et al., "The cost of pension insurance," Journal of Risk & Insurance; vol. 69, No. 2, p. 121-170, Jun. 2002.

List of Diagnosis Related Groups (DRGs), FY 1995: http://www.hcfa.gov/stats/drg95dsc.xls.

R.F. Averill et al., "Development and Evaluation of Clinical Risk Groups (CRGs) HIS Research Report." Sep. 1999, http://www.hcfa.gov/stats/ss95both.xls.

Mark S. Blumberg M.D., "Maryland Mortality for Non-Elective Surgery: A Prototype Ramo System," May 6, 1987.

D.L. Dunn et al., "A Comparative Analysis of Methods of Health Risk Assessment Final Report," Society of Actuaries, Dec. 21, 1995.

G. Thomas Ray et al., "The Cost of Health Conditions in a Health Maintenance Organization," Medical Care Research and Review, vol. 57, No. 1, pp. 92-109, Mar. 2000.

Mark S. Blumber, "Potentials and Limitations of Database Research, Statistics in Medicine," vol. 10, No. 4, p. 637, 1987.

Annemarie V. Wouters, "Disaggragated Annual Health Services Expenditures: Their Predictability and Role as Predictors," Heath Services Research vol. 26, pp. 247-272, Jun. 1991.

G. Binns et al, "Extracting More Profits from Small Group Renewals presentation to Conseco Health," Dec. 7, 1999.

G. Binns et al, "Mining the Data for Smarter Renewals presentation to Fortis," Nov. 15, 1999.

"Medical Scientists Inc. Selects MEDSTAT for 3 Year Data Agreement," PR Newswire, p. 7992, Jul. 26, 2000.

* cited by examiner

COMPUTERIZED MEDICAL UNDERWRITING OF GROUP LIFE INSURANCE USING MEDICAL CLAIMS DATA

CROSS-REFERENCE TO RELATED APPLICATIONS

This application claims the benefit of U.S. Provisional Application No. 60/701,311 filed on Jul. 21, 2005, which is incorporated by reference in its entirety.

BACKGROUND OF THE INVENTION

1. Field of the Invention

The present invention relates to a new technology to underwrite group life insurance. In particular, the present invention relates to predicting the expected claims to be made by a group based on pooled historical data of claims for life insurance and pooled historical data of medical claims.

2. Background Art

Group insurance for Life Insurance (life) for employees is widely available. In order to set appropriate premiums for these risks it is necessary to estimate the likelihood of the insured events (number of deaths) and the severity (or cost) of each event, for each insured group. Because of the relative rarity of these events for life, the experience of a group is too small to provide reliable estimates for any but the largest groups (e.g., with ten thousand or more employees).

The following is an example illustrating the risk profile presented by groups of modest size, in this case for a group of 500 employees. It assumes that the binominal distribution is an accurate representation of the likelihood of death. A 90% confidence interval is calculated. The following table lists the range of number of life claims in the confidence interval at 3 different probabilities for the event.

TABLE 1

Confidence Interval Example

| Probability | 90% Confidence Interval | |
|---|---|---|
| | Lower Bound | Upper Bound |
| .001 | 0 | 2 |
| .005 | 0 | 5 |
| .010 | 2 | 9 |

If a group has 2 events, it is in the 90% confidence interval for probabilities 0.001, 0.005 and 0.010 or a potential range of a 10-fold difference in true underlying probabilities for the event. This could result in a 10-fold difference in premium. If 0 or 1 event occurs, the underlying rate could be a 0.001 or 0.005 or a 5-fold difference in the true probability. Therefore, refined analytic methods are needed for accurate premium rate settings to reflect the group's underlying risk since the 5-fold or 10-fold difference in risk would turn into a 5-fold or 10-fold difference in insurance premium. The 5-fold or 10-fold range in risk and premium should be unacceptable to both the insurer and the insured.

The alternative actuarial approach uses estimates of group risk based on the age and gender (demographics) of each group's employees by using tables based on data pooled from many groups (i.e., manual rates). Assume for example, the likelihood of a 20 year old male dying in a year is about $1/1,000$ and the likelihood for a 62 years old male is about $10/1,000$. The group risk is calculated by summing each eligible employee's demographic risk, the sum being the group's base risk. The group's experience may be used to adjust (usually done via a weighted average) the demographic risk higher or lower, depending upon the historical experience. While the demographic incidence rates may be modified by the industrial codes and geographic location of specific groups they do not specifically adjust for the considerable variation in the underlying morbidity of employees which underlies the risks of life claims.

The experience based rates adjust for the historical or backward looking component of underlying morbidity but do not provide an accurate estimate of the future morbidity risk for modest size groups.

Accordingly, there is a need for underwriting methods that address groups of modest size and accounts for the underlying morbidity of the employees making up a group.

BRIEF SUMMARY OF THE INVENTION

In order to improve measuring risks of death for each insured group of employees, the present invention develops methods for achieving the following:

1. Providing standards for the probability of having a claim for death based on pooled historical life claims data, that include disease and injury specific data, measured against pooled medical claims data.

2. Providing expected costs or indexed cost of life claims based on a standard unit or index value that can be scaled to the appropriate payment amount if death occurs during the policy period.

3. Applying 1 and 2 above to the recent medical claims data for each insured employee group to estimate its current risks for life.

One benefit of this invention over traditional actuarial methods is to calculate group premium rates that are more accurate than premium rates derived from manual, experience or combined manual with experience based underwriting. The present invention develops a morbidity structure and applies quantitative algorithms or statistical models to the medical claims data for individuals in a group. The results include predicted incidence rates of life and predicted cost for the claim. The result of the application of this invention is a more accurate estimate of the group's predicted exposure for life insurance than is available through traditional methods.

Individual life insurance policies are frequently underwritten using the results of a medical exam including hematology analysis, urine analysis, vital signs, history and electrocardiogram. These costly exams are used to more accurately assess and price life risk than can be done using demographics alone. The life insurer wants to avoid anti-selection where people with greater risk than average apply and obtain insurance coverage without a corresponding increase in premium. This approach is rarely used in the group market due to its cost, intrusiveness and lack of group level benchmarks or algorithms for aggregating results to the group level. Current individual life insurance underwriting uses different measures of morbidity (e.g., lab results) and different algorithms for pricing coverage.

Still further benefits and advantages of the invention will be apparent to the skilled worker from the discussion that follows.

DETAILED DESCRIPTION OF THE INVENTION

I. Incidence Rate Calculations for Life Insurance

Although the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated. Accordingly, "life" risk is used to refer to the probability of death occurring during the policy period. "Life claim" and "death" may be used as synonyms since a life claim results from a death.

It is to be further understood that the titles of the sections of the specification, including but not limited to "Detailed Description of the Invention", relate to a requirement of the United States Patent and Trademark Office, and are not intended to, do not imply, nor should be inferred to limit the subject matter disclosed herein or the scope of the invention.

Figure 1:
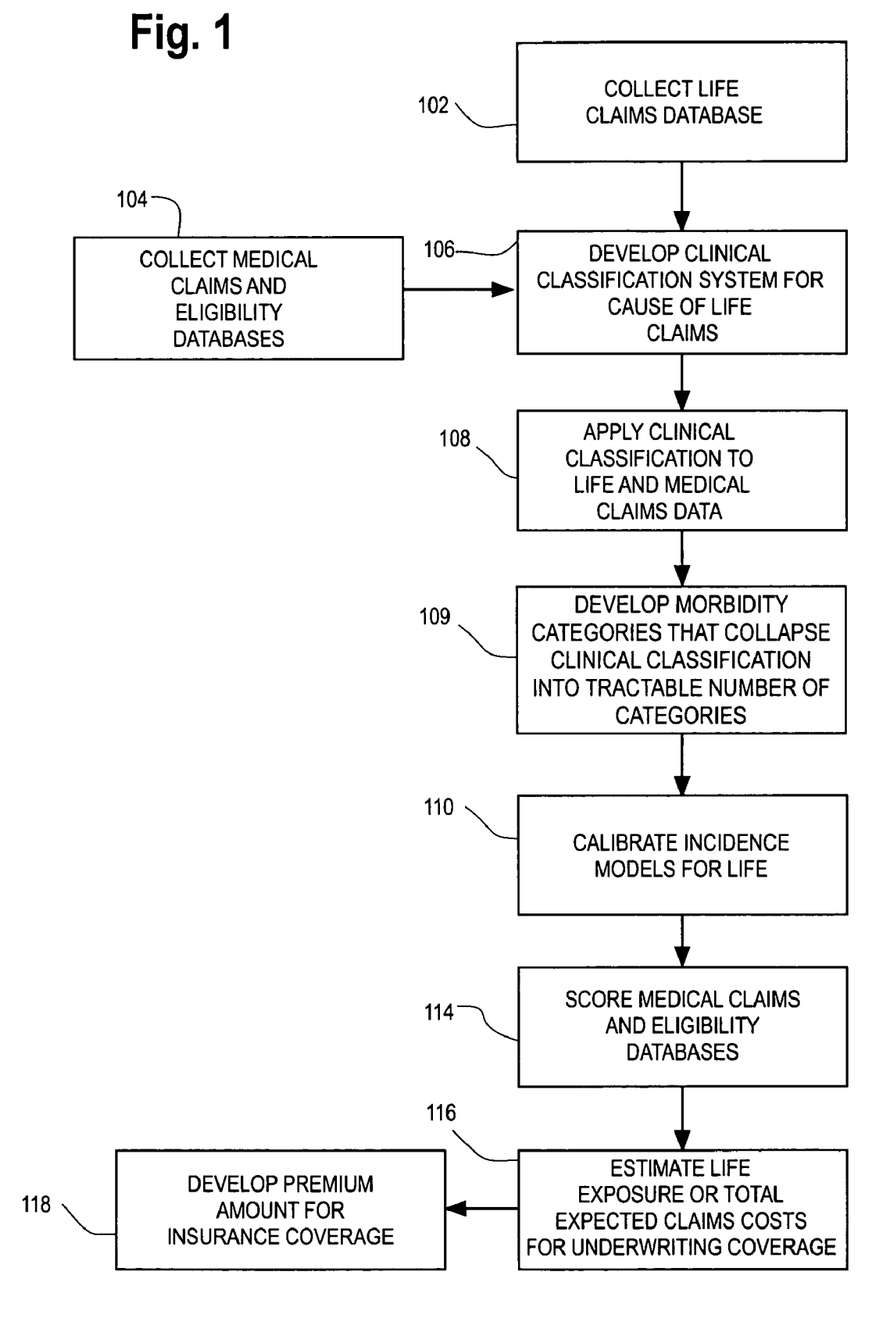
FIG. 1 is a flowchart of an embodiment of an overview of a method for estimating future life claim costs and pricing the associated insurance premium for coverage.

Referring to FIG. 1, an exemplary embodiment of the present invention collects life claim information (box 102) and also collects medical claims information (box 104). A clinical classification system is developed for the cause of the life claims in the database (box 106) and applied consistently to both the life claims and the medical claim data (box 108). The clinical classification system is then collapsed into a more tractable number of categories, called morbidity categories, in order to get more stable incidence rate estimates (box 109). Models for the incidence of life claims are calibrated (box 110). The medical claim and eligibility databases are then scored (box 114). The results of that scoring can then be used to estimate the number and cost of expected claims which can be used to estimate total expected claims costs or life exposure (box 116). The results of the scoring can then be used to determine pricing for life coverage (box 118).

This invention uses an alternative approach to traditional experience or demographic based underwriting. This invention can use life claims data (particularly diagnostic information—see box 102 in FIG. 1 regarding life claims data and below for exemplary data layout in Table 2) as a first database or life claims database.

TABLE 2

Sample Life Data Layout

| Variable | Type | Format |
|---|---|---|
| sex | Char | $4.00 |
| Dx1 principal | Char | $6.00 |

TABLE 2-continued

Sample Life Data Layout

| Variable | Type | Format |
|---|---|---|
| cause death | | |
| Dx2 secondary | Char | $6.00 |
| cause death | | |
| Dx3 tertiary | Char | $6.00 |
| cause death | | |
| patdob | Num | YYYYMMDD |
| Death date | Num | YYYYMMDD |
| Reported date | Num | YYYYMMDD |
| Paid date | Num | YYYYMMDD |
| age | Num | 3 |
| male | Num | 1 |

Where sex is the gender of the subject, Dx1 (ICD-9 code) is the diagnosis that was the principal cause of death, Dx2 is the diagnosis that was the secondary cause of death, Dx3 is the diagnosis that was the tertiary cause of death, patdob is the claimant's date of birth, Death date is the date of the death, Reported date is the date the death was first reported, Paid date is the date the death claim was paid, age is the age of the claimant and male is 1 if male claimant and 0 otherwise.

Medical claims data must include computerized diagnostic information to augment demographic data—see box 104 of FIG. 1 and below for exemplary data layout in Table 3 (or medical claims database) and Table 4 is a second database (or medical enrollment database).

TABLE 3

Samples Medical Claims Variables (Employees Only)

| Variable | Type | Format |
|---|---|---|
| group | Char | $14.00 |
| personid | Char | $20.00 |
| DX1 | Char | $6.00 |
| DX2 | Char | $6.00 |
| DX3 | Char | $6.00 |
| DX4 | Char | $6.00 |
| DX5 | Char | $6.00 |
| Paid date | Num | YYYYMMDD |
| Incurred date | Num | YYYYMMDD |

Where group is the employer ID, personid is the employee's ID, DX1-DX5 are up to 5 ICD-9 code diagnoses with the decimal that are associated with that employee's claim, Paid date is the date the claim was paid and Incurred date is the date that the service was incurred. Appendix 1 contains an example SAS data standardization program for a typical medical claims database that includes charges, payments and other variables not required for this invention but are typically included in medical claims data files.

TABLE 4

Samples Enrollment Variables (Employees Only)

| Variable | Type | Format |
|---|---|---|
| group | Char | $14.00 |
| SEX | Char | $1.00 |
| personid | Char | $20.00 |
| PATDOB | Num | YYYYMMDD |

Where group is the employer, SEX is the gender of the employee, personid is the employee's ID number and PAT- DOB is the employee's date of birth. Note that dependents may need to be screened from the eligibility file since they are typically not covered under group life policies.

The present invention does not require that these databases be linked at the person level but nevertheless may be practiced with some or all of the data being linked, though with all the data linked other methods would probably be used by those of ordinary skill in the art. A practicable exception is for the group and employee linkage between the medical claims and eligibility file as per the data in Tables 3 and 4 above, but with no linkage between Table 2 and Table 3 or 4. In other words, a large life claims database can be used with a large medical claims database possibly from a separate population to develop incidence rate models for life claims.

To facilitate the collection of medical data as exemplified by box 104, below is a sample program to standardize life medical claims data with ICD-9-CM (or 10) codes (the standard for U.S. medical, life and disability insurers for coding the cause of a claim, and these data can be 5 digit or 3 digit ICD codes). Other coding or medical classification systems also exist, e.g., SNOMED. For the purposes of the present invention codes like ICD-9-CM or ICD-10, SNOMED, or other systems that are used to categorize medical conditions are referred to as medical condition codes or medical diagnosis codes or, for shorthand, medical diagnoses.

The data can be read from an Excel spreadsheet, for instance, to be analyzed in a computer system coded to implement the present invention. One system that can be used to implement the present invention is the commercially available statistics program SAS produced by SAS Institute of Cary, N.C. The input data are converted to the format needed (i.e., standardized) by the analysis system and variable names from the life claims database are mapped to standardized names utilized by the analysis system. In the present examples, the medical condition codes used by the analysis system are modified ICD-9-CM codes, but other code systems or modifications of the ICD-9-CM system may be used.

Data can be validated by comparing summarized data from the medical claims and life claims to control totals (e.g., total number of records, number of claims, total claims paid, etc.) and other summary reports developed by the organization supplying the data—standard computer processing techniques for validating accurate data transfer and reading. The data can also be standardized into common units such as date format, level of medical condition code used (e.g., for ICD-9, 5 digit, 3 digit, subchapter grouping) and currency units.

A universe of claims eligible for analysis and use in the database can be defined and used to create and calibrate the life prediction models. A universe of eligible claims can exemplarily comprise data such as date range for claims, the covered person's age and gender, and the covered person's employment status. When each source is complete the files can be concatenated into one file.

Continuing the discussion of box 104 in FIG. 1, in Appendix 1 is a SAS program for medical claims data to standardize its format for processing. Each source of data may have a different layout. The medical claims data can be validated, cleaned and then standardized.

A universe is defined and data that have similar formats from different sources can be concatenated into one file for summarization and analysis.

The coding of the medical claims and life claims with medical condition codes should be at the same level of specificity, and as indicated earlier, is not limited as to form. The medical condition coding system can have different levels of specificity, and may be hierarchical in nature such that a higher level of a hierarchy may subsume multiple elements of a more detailed hierarchy below. Where medical claims data and life data are not in a consistent format, but can be mapped onto the same system, where the system mapped to is hierarchical the coarsest level may need to be used for comparability across data sets. Additionally, common but inconsequential diagnoses will be ignored in the medical claims when the life claims data do not contain that level of detail, that is to say that while a condition may be categorized for medical care purposes, it has no presence in databases tracking causes of life.

The medical claims and life databases are usually from different populations. The resulting morbidity based life incidence models are then applied to different groups' medical claims data to produce expected life exposure for underwriting life insurance. This refined estimate of claim frequency and severity can then be used in estimating the costs associated with insurance coverage and accordingly pricing the insurance coverage.

The morbidity model based insurance premium pricing can be an adjustment of the traditional demographic or experience based methods used by actuaries and underwriters or derived separately using exposure data and actual claims experience. Life cost and total exposure estimates derived from the medical claims data for pricing life will be described later.

Often, the age by gender specific incidence of medical conditions or morbidity can be similar in the insured populations of employees for both the medical claims database and the life claims database, and incidence rate estimation can be done on that basis.

Large life and medical claim files help assure that they are more likely to have similar morbidity patterns (within age by gender strata) than smaller, more selective files.

Use of standard Society of Actuaries (SOA) age by gender standards to estimate life claim risk also involves a similar operating limitation; specifically, that the morbidity pattern in the population used as the SOA standard is similar to the life insured population being priced. This is because morbidity of the insured population drives the system, not age or gender of the insured population directly.

Under the conditions of similar proportions of medical conditions (within age by gender) for the medical population and the life population, the relative incidence rate can be calculated for such conditions using conditional probabilities or similar measures. Traditionally, the incidence rate for life is the number of life claims in a year divided by the number of insured people and stratified by combinations of age, gender, occupation and other factors related to life claims. However, these calculations of incidence rates are not done by morbidity condition with current underwriting procedures for groups.

This method and system of the present invention calculates the incidence rates conditionalized on morbidity condition can be calculated in addition to demographics and other factors. While any conditional probability estimation method can be adapted for the practice of this invention, Bayes Theorem is used for the preferred embodiment of this invention:

$$\text{Probability}(A \text{ given } B) = \frac{\text{probability}(B \text{ given } A) \times \text{probability}(A)}{\text{probability}(B)}$$

This calculation is normally done within an age by gender strata, but the calculation can also be applied to data having morbidity information that has not been stratified. A concrete example is provided below. For life insurance:

Probability (death given diagnosis Y)=probability (diagnosis Y given death)* probability (death)/probability (diagnosis Y), where the probability (diagnosis Y given death) equals the proportion of life claims resulting from diagnosis Y (a morbidity category), the probability of diagnosis Y equals the proportion of the insured population with diagnosis Y, and the probability of death is the death rate for the age by gender strata for a large insured population with similar characteristics.

The following table is a hypothetical example of a Bayesian calculation for the probability of death for a male 55-64 years old with lung cancer. Assume the following: lung cancer is 5.0% of death claims for males 55-64 (=probability (B given A) from equation above); the probability of death is 0.007 for 55-64 males during the next year (=probability (A) or the prior from equation above) and the probability of lung cancer for males 55-64 is 0.6% (=probability (B) from equation above). This results in a Bayesian probability estimate of 0.058335 (=probability (A given B) from equation above) or the probability of a life claim given lung cancer is 5.8% using these calculations, as shown in Table 5.

TABLE 5

Male 55-64

|  | Death | Medical |
|---|---|---|
| Lung cancer count | 60 | 70 |
| Total count | 1200 | 11667 |
| % | 5.00% | 0.60% |
| Prior probability of death male 55-64 | 0.70% | |
| Bayesian probability = (.05*.007)/.006 | | |
| Bayesian probability (death given lung cancer) = 0.058335 | | |

Therefore, the probability (death given diagnosis Y) can be calculated using readily available medical and life insurance claims data. This is the fundamental building block for calculating morbidity based death rates.

A more general alternative to Bayes Theorem for calculating conditional probabilities is a Bayesian Network where Bayes Theorem is applied multiple times in the context of a decision tree, conditionalizing the probability on variables such as age, gender, standard industry classification code (SIC code) of employer, occupation, geographic region, company size and experience and other factors in addition to the morbidity. Graph theory (especially directed or acyclical graphs), Monte Carlo simulations and other techniques can be used to calculate the joint and conditional probabilities needed for predicting the incidence rate of life claims for individuals and groups of employees. The result of these joint and conditional probability calculations is a look-up table of incidence rates that is used to score each person in a group. The person's characteristics are classification factors for the table and the associated incidence rate for life is a predicted conditional probability that is looked -up in the appropriate cells of the table.

Figure 2:
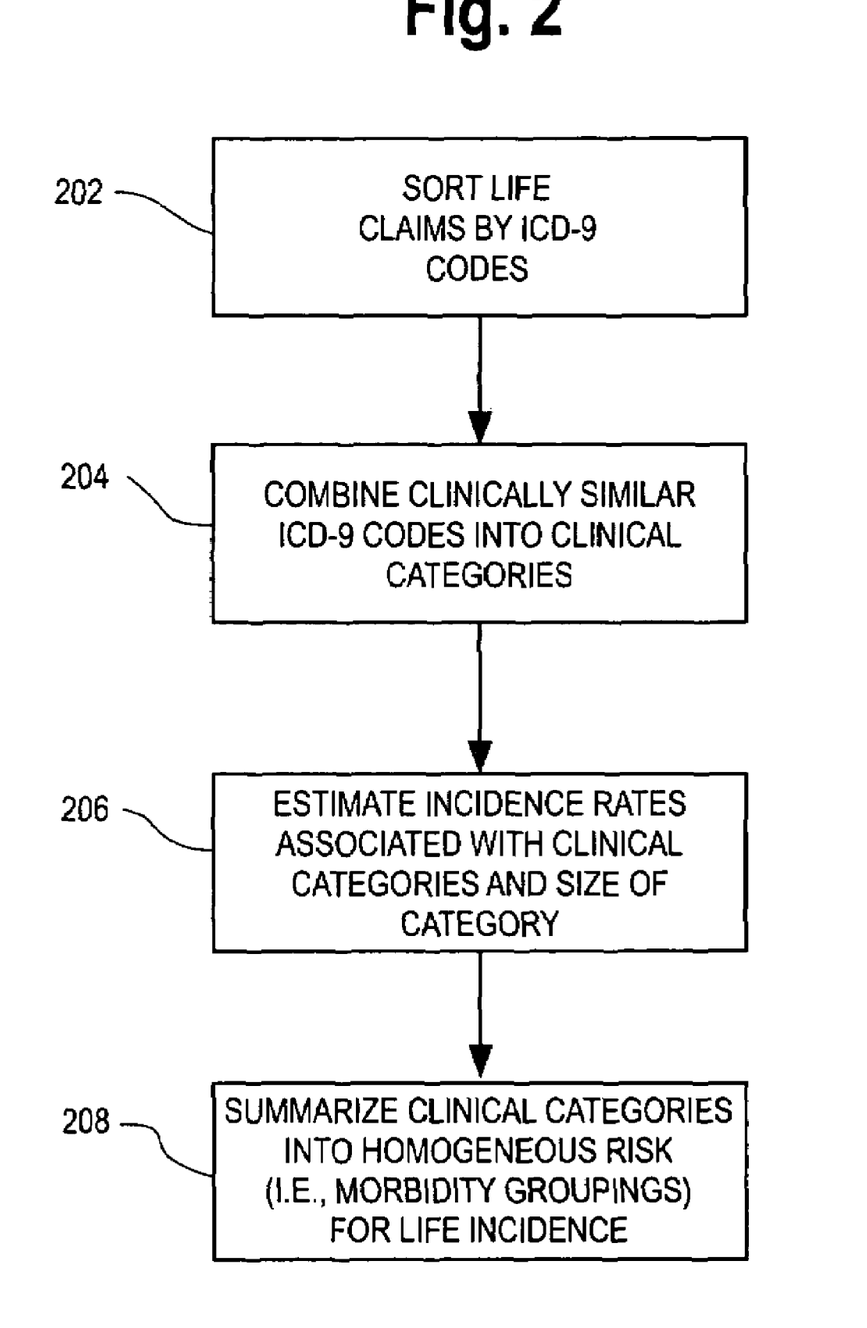
FIG. 2 is a flowchart of an embodiment of a process for developing a morbidity classification system for life claims. It details boxes 106, 108 and 109 of FIG. 1.

Referring to box 106 of FIG. 1, the preferred embodiment uses groupings of ICD 9-CM (or 10 or other coding schemes) diagnosis codes to define morbidity categories. The coding system should be the same for medical and life claims or be able to be mapped uniquely onto a common coding system. The exemplary embodiment of the present invention uses ICD-9-CM, the present industry standard coding system. However, the present modeling approach can be applied to other classification systems with just as much validity. The accuracy of the present modeling approach will be dependent upon the accuracy of the classification system, the coding accuracy, the representativeness of the sampled population and the amount of data available for model calibration. The morbidity categories should be homogeneous (see boxes 204 and 206) with similar likelihood of leading to death. Non homogeneous categories can be used if the likelihood of death is similar by medical condition code within the category. The objective is to develop morbidity categories that are clinically similar or at least have similar risk (e.g., Bayesian probability of the insured event) and are large enough to lead to robust estimates of the incidence.

A life insurer typically does not have medical information on a large portion of its insured customers so the conditional and joint probabilities cannot be calculated directly. This invention's preferred embodiment calculates the probability (death given diagnosis Y) directly using the definition of a conditional probability when appropriate data are available (medical and life claims are linked at the person level) and using a technique such as Bayes Theorem or Bayesian Networks when the data do not support a direct calculation of the conditional probability. A simple example has 10,000 males 55-64 covered for medical and life. 6 of those males covered have life claims from lung cancer and a total of 100 have lung cancer as a medical condition, resulting in a conditional probability of 6/100 or 6% of having a life claim given that you are a male 55-64 and have lung cancer.

Referring to box 109 in FIG. 1, the medical and life claims are classified by morbidity category. The following is one simple example describing using a listing of ICD-9 codes as one possible definition of the lung cancer morbidity category. Other definitions may be used also or the category combined with other cancers, etc. The number is the ICD-9-CM diagnosis code and the following text is an abbreviated name (MAL or MALIG "malignant", NEO means "neoplasm", NEC means "Not Elsewhere Classified", and NOS means "Not Otherwise Specified") of the site of the lung cancer.

162 MAL NEO TRACHEA/LUNG*
1622 MALIG NEO MAIN BRONCHUS
1623 MAL NEO UPPER LOBE LUNG
1625 MAL NEO LOWER LOBE LUNG
1628 MAL NEO BRONCH/LUNG NEC
1629 MAL NEO BRONCH/LUNG NOS
164 MAL NEO THYMUS/MEDIASTIN*

The calculation using Bayes Theorem of the probability (death given diagnosis Y) equals the (proportion of the life claims with diagnosis Y as the cause—calculated from the life claims file) times the (overall incidence of death) divided by the (probability of diagnosis Y) which equals the proportion of people with diagnosis Y in the medical claims database.

Referring to box 110 in FIG. 1, the proportion of people with diagnosis Y is calculated as the number of people with a medical claim of diagnosis Y divided by the total number of people enrolled for medical coverage. When the medical claims and life claims are directly linked by a unique person level identifier (from the same pe rson) the conditional probability can be calculated directly using the formula Probability (death given diagnosis X)=Probability (death and diagnosis X)/Probability (diagnosis X)

This is the preferred embodiment when the data are linked at the person level although such data are rare, and the invention can be used where such data is not linked at the person level.

Calculations are typically done using age ranges (frequently 9 ranges of 5 years, such as 20-24 (or 18-24), 25-29, . . . , 60-64 by male/female) for groups of insured employees. This process makes an array of boxes, one axis being diagnosis, and the other an age range (see Table 6 for an example).

TABLE 6

| General Category for Incidence Rate Calculations | Age 18-24 | Age 25-29 | Age 30-34 | Age 35-39 |
|---|---|---|---|---|
| Infectious diseases | 5 | 52 | 33 | 10 |

Estimates of the Bayesian or conditional probability of death given a diagnosis X are calculated for a set of morbidity conditions within each age by gender strata. The number of morbidity conditions that are useful will be driven by the number of life claims by strata and the frequency by morbidity conditions. Fewer than 5 claims per age by gender strata or cell is not very credible for probability calculations. At least 10 claims per cell are recommended; however, adjacent ages or gender can be combined for greater counts, providing greater rate stability if they have similar underlying distributions. For example, sometimes you merge two or more adjacent but not credible boxes to make a contiguous credible box. Table 7 shows two generic cases, and Table 8 shows a concrete example of merging categories from Table 6.

TABLE 7

|  | Age 1 | Age 2 | Age 3 | Age 4 |
|---|---|---|---|---|
| male |  |  |  | Merged gender example |
| female |  | Merged adjacent age example |  |  |

TABLE 8

|  | General Category for Incidence Rate Calculations | |
|---|---|---|
|  | Age 18-24 and Age 25-29 | Age 30-34 and Age 35-39 |
| Infectious diseases | 57 | 43 |

The enrolled medical population with medical claims typically will be larger than the life claims file since the frequency of employees incurring one or more medical claims in a year is about 600-800/1,000 enrollees per year versus 1-10/1,000 enrollees for death per year. Therefore, definitions of morbidity conditions producing credible probabilities within the life files usually provides credible probability estimates in the medical claims calculations since the higher frequency of medical claims than life claims gives larger number of cases and more credible estimates of incidence rates.

Box 206 of FIG. 2 and the table for Males 55-64 with EP 180, and lung cancer illustrate Bayesian probability calculations. This example is based on disability rates but the application to death rates is obvious to one skilled in this art. When the incidence rates of death are different for similar conditions, those conditions should be put into separate morbidity categories for predicting future life claims for underwriting (see box 208).

Many life claim files have a single medical condition code as a cause of death. People in medical plans may have numerous diagnoses in a year. (Note that one year is used in this invention as the standard contract time period for pricing and rate estimation even if the insurance contract is for a different time period since one year eliminates seasonality and most claim files have observations based on groups enrolled for multiples of a year but other time periods can be used by rescaling all of the calculations.) If the life claims file has multiple codes, then morbidity categories can be defined as combinations of multiple medical condition codes. Otherwise, there will be multiple morbidity categories associated with individuals in the medical claim files and only one morbidity category associated with the life claim.

This potential multiple counting of individuals or morbidity categories can be adjusted for in many ways. The most straightforward adjustment is to assume the highest probability morbidity condition only for an individual. One alternative is that all morbidity conditions can be used and assume statistical independence between the conditions. The overlap between the pairs, triples, etc. of morbidity conditions needs to be calculated so that they are not double counted. The following is a general formula for calculating the union of independent events A1 through An.

$$P(\cup A_i \text{ for } i=1, \ldots, n) = \Sigma P(A_i) - \Sigma_{ij} P(A_i \cap A_j) + \Sigma_{ijk} P(A_i \ldots \cap A_j \cap A \ldots _k) - \ldots + (-1)^{n-1} P(\cap A_i \text{ for } i=1, \ldots, n)$$

If the morbidity conditions have a positive interaction with one another (the likelihood of death is greater than the sum of the parts) then double counting would be a more accurate estimate of the probability of a life claim than the union of the probability assuming statistical independence.

The preferred embodiment of this invention normalizes or sets the estimate of the total number of expected life claims for a large block of business (e.g., all groups in a large medical plan) to the expected number of claims for that block calculated using a traditional actuarial model driven by demographics and other non-morbidity factors. Morbidity categories with few or no life claims can be omitted. The method used for adjusting the multiple morbidity conditions in the medical claims will not have any influence on the total expected number of life claims for the block of business if the block is set to equal the number of expected claims from the demographic model. This assumption is not necessary but can be made. However, there could be large differences at the person and group levels.

Figure 3:
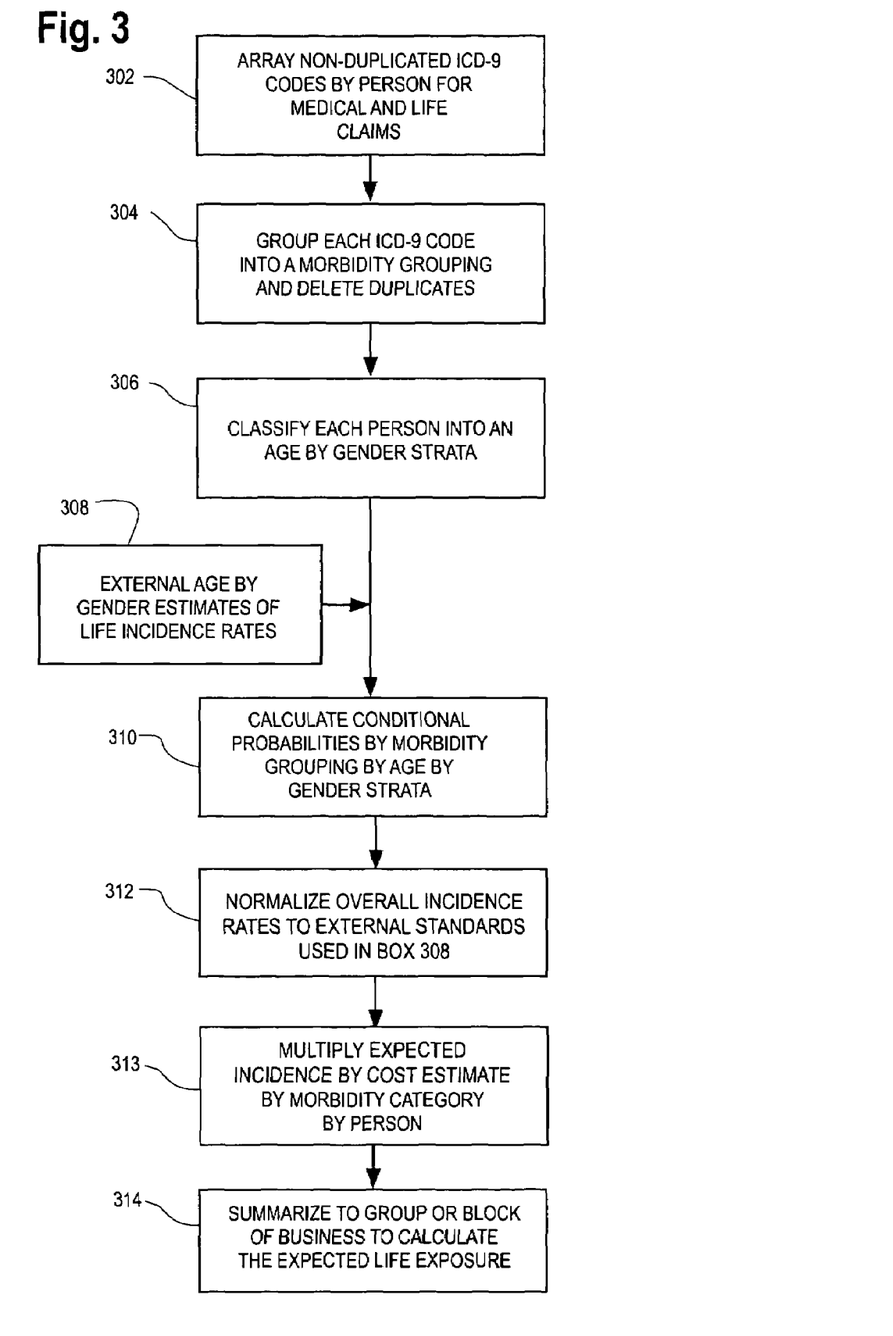
FIG. 3 is a flowchart of an embodiment for applying the morbidity classification system of cause of death to calculate incidence rates for life claims using medical claims data for underwriting groups and life claims databases for calibrating the life risk factors. This details boxes 110 of FIG. 1.

The medical condition codes for a person with medical claims are combined into a non-duplicated array covering a fixed time period such as a year (see box 302). Each distinct medical condition code is then classified into a morbidity category and duplicates of each category are dropped (see box 304). All people in the eligibility file, including those with and without medical claims, are also classified into age by gender strata regardless of whether they have a medical condition code (see box 306). External age by gender rates of death (see box 308) may be used to calibrate the overall incidence rate estimates to established standards. Those rate estimates are used in the numerator of the Bayesian probability calculations as the prior probability of death (see box 310).

A normalization of the incidence rates for life insurance (see 312) is done by age by gender strata across all morbidity categories by setting the total estimate for the morbidity model for each demographic stratum for a block of business to equal the total estimate from a demographic model for the same demographic strata. In other words, the normalization is a simple, proportionate adjustment increasing or decreasing the morbidity model prediction so that the number of expected life claims from the morbidity model equals the expected number of life claims from the demographic model for a large book of business. Dividing the demographic estimate by the morbidity estimate produces the normalizing factor that will equalize the morbidity and demographic model estimates. This factor is then multiplied by each morbidity incidence rate estimate. This equalizes the morbidity and demographic incidence rates for the entire block of business by demographic strata but allows individual group estimates to vary substantially. The strata and categories may be very fine or to only a few rates, depending upon the accuracy and amount of data. This normalization is not necessary but optional.

Life Insurance Claim Cost

Life insurance typically consists of a single payment that is usually a multiple of the employee's salary. If the proportion of life claims by morbidity category varies substantially by salary, then multiple sets of conditional probabilities may need to be calibrated on life claims data stratified by salary level. Otherwise, an index value, such as the multiple of salary that is the life insurance coverage, can be used for the cost of the life insurance claim. The index value is then scaled by the salary or other factor that will translate the index amount into the life insurance liability in dollars. If life claims are not paid quickly, discounting may be used to provide a more accurate estimate of the life insurance liability to the insurer. Discounting is performed using standard actuarial techniques for discounting future payments.

The discounted expected claim cost and the incidence rate from the Bayesian probability model are calculated for each separate morbidity category for each person (see box 313). The expected cost is multiplied by the Bayesian probability to calculate the total expected discounted cost for that morbidity category for that person. Each person's expected discounted exposure by morbidity category (product of probability times cost) is summed to calculate that person's total expected discounted exposure for the preferred embodiment. The objective is to provide the most accurate estimate of life claims cost for the group for use in setting the premium.

Calculating Person and Group Level Expected Life Claims Costs

Referring to boxes 114 and 116 of FIG. 1, in order to price the insurance, an expected claim cost or life exposure must be calculated. Estimating the probability of a person having a life claim is done by "scoring" the medical claims data (see also FIG. 4). A person level file is prepared that includes the person's age, gender and morbidity grouping(s) from the medical claims. The preferred embodiment uses a look-up table to associate the morbidity grouping(s) by age by gender strata (alternatively other factors such as company SIC code, geographic region and others can be applied) with the probability of death (see box 402). Multiple look-up tables may be required if alternative insurance options are required for pricing the life coverage. For example, the occupation may have a large impact on the probability of death. Therefore, different incidence rates by demographic strata should be used in the Bayesian probability calculation if sufficient data are available for accurate rate estimates and scoring by occupation. If death rates by occupation are not credible, then occupational categories need to be collapsed to produce stable death rate estimates.

Figure 4:
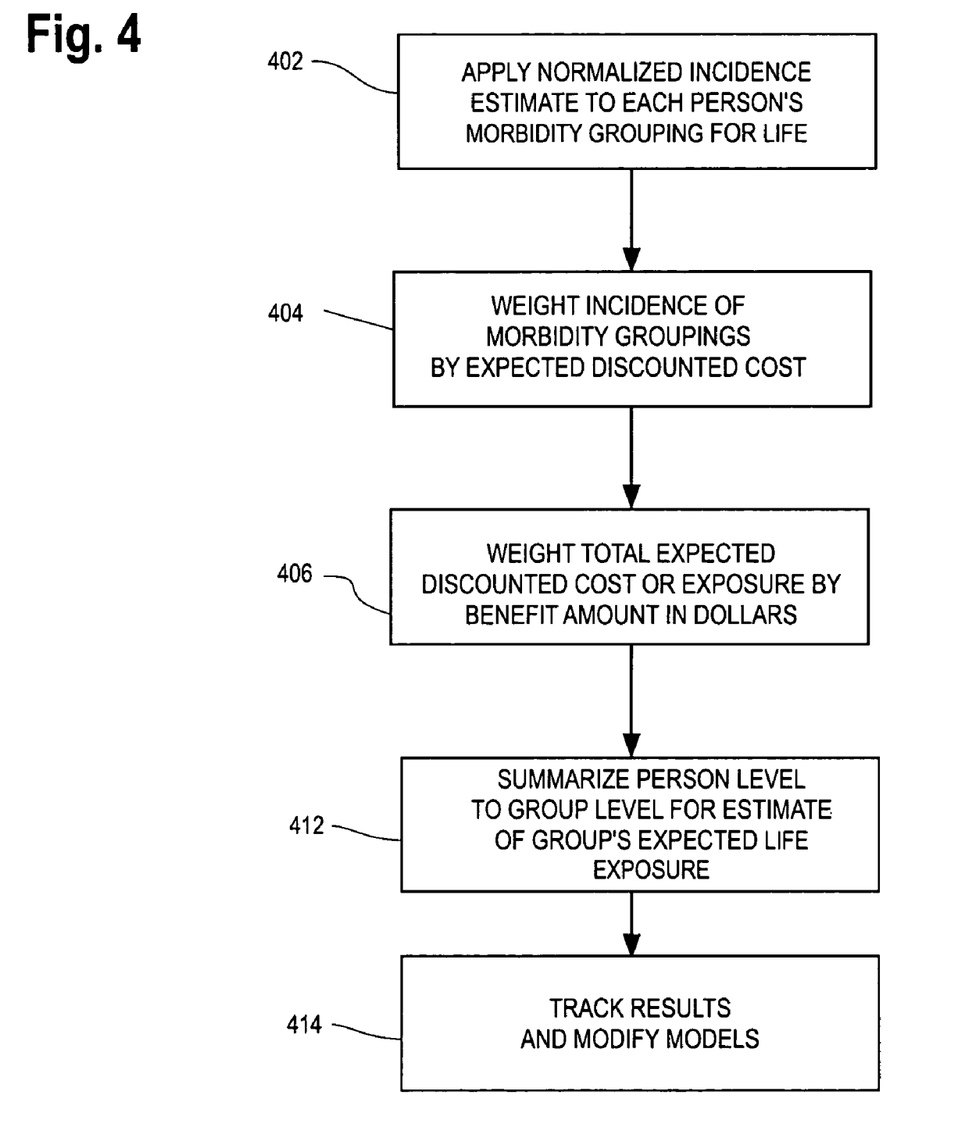
FIG. 4 is a flowchart of an embodiment for estimating each eligible person's expected life claims and combining those estimates into a group level estimate of its claims cost and details boxes 114 and 116 in FIG. 1.

Each person with morbidity grouping codes found associated with death is scored by looking up the probability of death associated with their demographic stratum and each of their morbidity grouping codes associated with death. Morbidity codes that are not associated with death in the life claim file may be assigned zero probabilities. Alternatively, the likelihood of death by accident, homicide or suicide can be calculated and allocated according to demographics of all eligible employees, replacing the zero incidence rates for people with no medical claims. If this approach is used, those morbidity categories should be removed from the conditional probability calculations to avoid double counting.

The likelihood (probability or incidence rate from box 402) for a morbidity grouping must be multiplied by the mean of the expected discounted cost (assuming the death occurs) to calculate the expected value of the discounted cost for a person with a morbidity condition (see box 404). This is the expected value in expected discounted cost for that person for that morbidity grouping. The preferred embodiment assumes a zero probability of a death claim from people with no diagnosis in the medical claims data other than from accident, homicide or suicide approach described above. Alternatively, the likelihood of sudden death from non-diagnosed morbidity may be estimated and included in the probability calculations. However, care must be taken to avoid double counting so renormalization of overall death rates to a large block of business may be required.

The preferred embodiment uses double counting of the probability overlaps when a person has multiple morbidity groupings—assuming that the events are additive but that the sum can be no greater than 1.0 (a certain event). The largest sum of probabilities for an employee is likely to be far less than 1.0. The expected claim cost is multiplied by the sum of the probabilities of his or her morbidity conditions leading to death in the next year. This estimate includes double counting for people with multiple morbidity conditions, as previously discussed. Therefore, the sum of all individuals' expected claim cost within a demographic stratum (e.g., males 18-24) for a large block of business may require recalibration to eliminate the double counting. One can normalize the morbidity model by multiplying each person's estimate by the ratio of the demographic stratum's estimate divided by the morbidity estimate for those within that demographic stratum, producing total expected morbidity claims costs equal to the entire block for that demographic stratum (see box 402). The ratio of an individual group's (e.g., an employer) demographic based expected claims cost divided by the morbidity model's expected claims cost is a measure of the relative morbidity risk for that group.

Actual underwriting results should be tracked over time and compared to the expected results. This information can be used to modify the incidence and cost models, especially for eliminating any systematic biases where the predictions are too high or too low (see box 116 in FIG. 1 and box 414 in FIG. 4).

Indication of a Price Quote and Morbidity Profile

The medical claims data and medical eligibility may not be sufficient to provide a final quote for life coverage since those files may not have an accurate census for life, indicate the amount of coverage such as average wages, show the group's life experience, or provide the industry type and occupation. However, a meaningful indication of the approximate proportion of the final quote to the current rates can be estimated by dividing the morbidity based estimate of claims costs by the demographic based estimate of claims costs (morbidity to demographic ratio).

This invention has an option of sending the morbidity to demographic ratio to the employer or broker representing the group. This indication would be sent to groups with morbidity to demographic ratio meaningfully below 1.0 along with a request for the information necessary to provide a final, binding life insurance quote.

In addition, a morbidity profile may be provided that compares the employer to a norm by morbidity category. The morbidity profile compares the percentage of employees with a morbidity condition that was used in the morbidity prediction model. The norm may be age by gender adjusted so that the employees' age or gender skew does not drive the differences. The objective is to provide information on morbidity conditions where the group may have an excess of morbidity so that disease management or other programs may be used to help reduce morbidity levels, thereby lowering the group's employees' risk of death. Morbidity improvement will lower future insurance costs and the employer's cost of turnover. Note that the conditions profiled are those morbidity conditions that are related to death rather than future medical expenses. Profiles of a group's frequency of actual morbidity groupings from the medical claims versus an average or standard may be provided to better understand the potential cost of death for a group or block of business.

Pricing Groups

Current actuarial estimates of risk frequently involve blending or averaging manual rates with experience based rates. Credibility theory is used to determine the weights assigned to each estimate. This concept can be generalized to include a morbidity based estimate of cost. The benefit of this approach is that the morbidity information is from details of the group's potential exposure while the manual rate reflects population averages and the experience provides information on the group's historical death rates. Weighting and combing these factors provides a unique estimate that should be more robust than estimates derived without the morbidity model's expectation.

Figure 5:
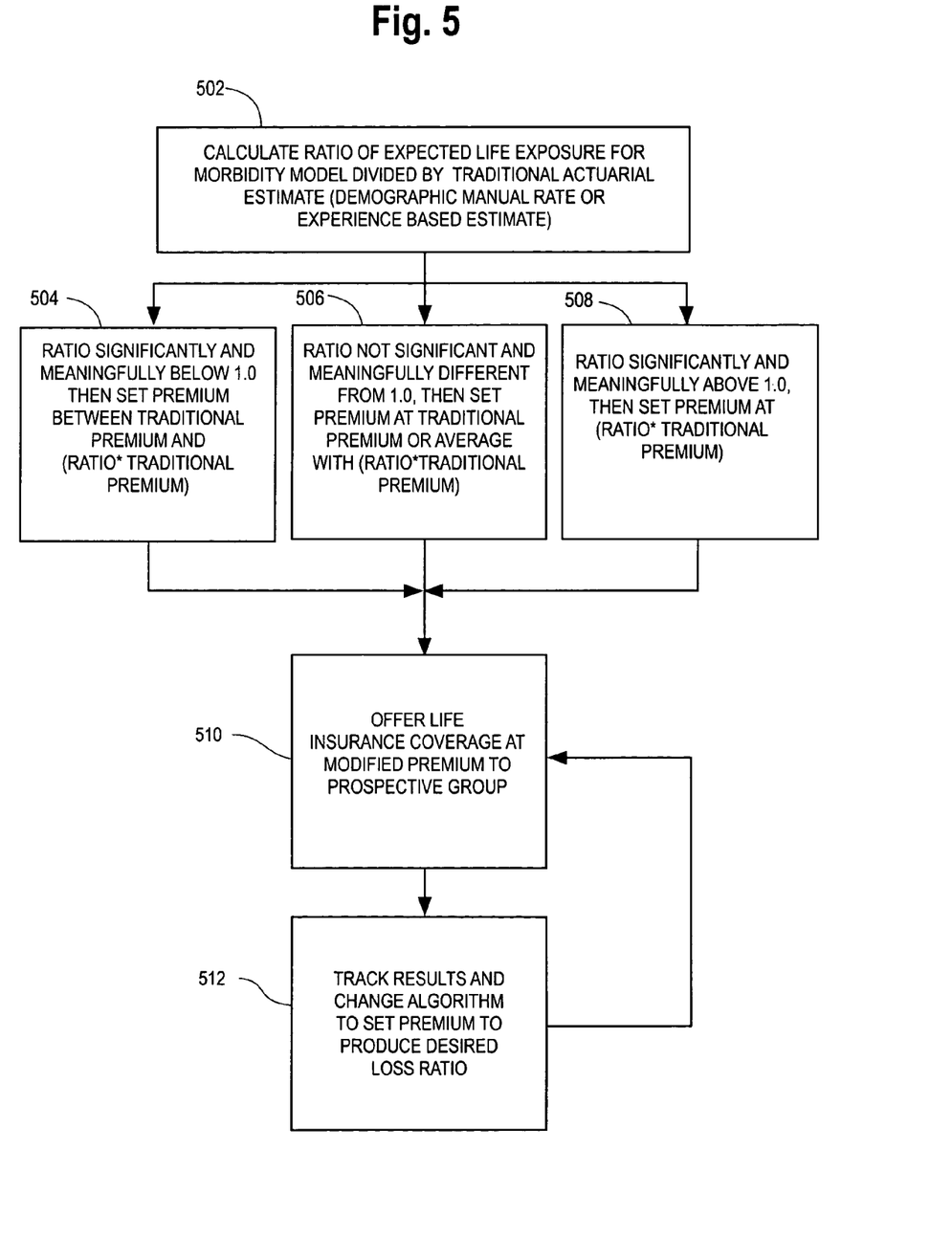
FIG. 5 is a flowchart of an embodiment of a method for using the expected exposure from the morbidity models to set a premium for pricing the life insurance coverage and it details box 118 in FIG. 1.

The morbidity to demographic ratio (i.e., morbidity model based expected claims cost divided by demographic model based expected claims cost) can be used to adjust the traditional premium to more accurately reflect the morbidity characteristics of the group and its associated claims costs (see box 118 in FIG. 1 and box 502 in FIG. 5). When the morbidity to demographic ratio is meaningfully greater than 1.0 (see box 508), the demographic characteristics do not entirely account for the group's morbidity risk so the premium should be raised. The traditional premium can be multiplied by the morbidity to demographic ratio. Alternatively, a weighted average of the two methods may be taken based on the credibility of the two methods used or another method for combining the two estimates may be used for estimating expected claim costs. The preferred embodiment gives 100% credibility to the morbidity to demographic ratio so the traditional premium is multiplied by the morbidity to demographic ratio. This will discourage groups from accepting coverage without paying additional premium to compensate for its morbidity risk.

Conversely, when the morbidity to demographic ratio is meaningfully less than 1.0 (see box 504), its morbidity risk is lower than its demographic risk. The ratio can be multiplied by the traditional premium estimate to produce the claim cost estimate. However, a smaller decrease may be enough price inducement to compel the customer to select this coverage over traditionally derived (and more expensive) premiums. For example, only half of the discount may be applied to the premium. Generally, the offered premium should be between the two estimates and this is the preferred embodiment.

Typically, many groups will have morbidity to demographic ratio that is close to 1.0 (see box 506). Those groups can be priced at the demographic based premium (manual rate) or a combination of the manual rate multiplied by the morbidity to demographic ratio or some other combination of the two factors.

Experience may be blended with the morbidity to demographic ratio. However, the confidence interval is frequently large so random variation may can be added to the cost estimate using experience. The preferred embodiment uses the experience to modify the morbidity to demographic ratio when the experience is worse than the upper bound of a large confidence interval (e.g., 90%).

An estimate of the variance of the group may be calculated as an additional pricing factor with greater variance implying greater risk and a higher price with all other factors being equal. The Lexian probability distribution can be used to calculate a confidence interval about the group or block's average expected death rate.

The Lexian distribution is somewhat more accurate than the binomial or Poisson distribution which could be used as alternative variance estimates. Larger confidence intervals for the expected claims cost imply a higher premium, all other factors being equal.

An alternative approach uses Monte Carlo simulation for estimating life pricing. The Monte Carlo simulation will calculate numerous random samples for a group using that group's morbidity categories and demographic stratification. The incidence rate for an individual will be 0 or 1, selected randomly in proportion to the morbidity incidence for that person's morbidity category by age by gender strata. If 1 is selected, then the expected claims cost is added to the groups sum of total expected claims costs. When zero is selected, zero expected claims cost is added to the sum of the total estimates for that group. The expected claims costs are summed for all people in that group. This process is repeated with random selections numerous times providing a distribution of expected claims cost for the group. This is the preferred embodiment for calculating the distribution of total life claims cost for a group or block of business.

The final step in the product is offering the insurance coverage to the group or its agent at the modified premium (see box 510). Results (e.g., loss ratios, acceptance of the insurance coverage) should be tracked and can be used to modify the algorithms for future policy offerings and premium rate setting (see box 512).

From the foregoing, it will be observed that numerous modifications and variations can be effectuated without departing from the true spirit and scope of the novel concepts of the present invention. It is to be understood that no limitation with respect to the specific embodiment illustrated is intended or should be inferred. The disclosure is intended to cover by the appended claims all such modifications as fall within the scope of the claims.

Each of the patents and articles cited herein is incorporated by reference as if fully set forth herein. The use of the article "a" or "an" is intended to include one or more.

APPENDIX 1

A sample SAS read program for medical claims using TruRisk's standard layout is below (see Box 104). Each client may have a different layout so the read programs will vary. The medical data are validated and then standardized. A universe is defined and data from different sources are concatenated into one file for analytics. A sample read and standardization for one source follows.

libname dat '.';

% let tpa = SOURCE;

run;

filename filein ("medical080204.ic.clm");

run;

```
title "&tpa test claims";
run;
data dat.claims;
infile filein lrecl=400 pad;
length group $14. EmpID $11. depid $2. clmno $10.;
input
@1 Group $11.
@12 EmpID $18.
@30 DepID $3.
@33 Clmno $19.
@52 Clmline $5.
@57 servDate mmddyy8.
@67 paidDate mmddyy8.
@77 Charge 17.
@94 Allow 17.
@111 Deduct 17.
@128 Copay 17.
@145 Coins 17.
@162 Payment 17.
@179 PPOSave 17.
@196 dx1 $5.
@201 dx2 $5.
@206 dx3 $5.
@211 dx4 $5.
@216 dx5 $5.
@221 CPT $5.
@226 HCPCS $5.
@231 AdjFlg $2.
@233 OrgClmNum $19.
@252 OrgChrgNum $19.
@271 pos $5.
@276 notALLOW 17.
@294 COB 17.
;
*Create unique identifier for a person for each group;
length personid $14.;
depid=translate(right(depid), '0', ' ');
personid=compress(left(EmpID)||left(DepID));
    if compress(clmtype) eq :**<<< select only medical; format paiddate servdate mmddyy8.;
run;
**validate and standardize;
data dat.claims dat.baddates dat.badempids;
    set dat.claims;
drop notallow pposave deduct;
allow=charge-notallow;
inelig=notallow;
discount=pposave;
deduct_c=sum(deduct,copay);
coins=.;
inpat=0;outpat=0;home=0;snf=0;urgent=0;er=0;ambsurg=0;
if compress(pos) in ('1', '01', '21', 'IH', 'I') then inpat=1;
if compress(pos) in ('2', '02', '22', 'OH') then outpat=1;
if compress(pos) in ('4', '04', '12', 'H') then home=1;
if compress(pos) in ('8', '08', '31', 'SNF') then SNF=1;
if compress(pos) in ('20') then URGENT=1;
if compress(pos) in ('23', 'ER', 'E') then ER=1;
if compress(pos) in ('24', 'ASC', 'B') then AMBSURG=1;
if servdate eq . or paiddate eq . then output dat.baddates;
else if empid eq ' ' or empid eq : 'UNEXP' then output
dat.badempids;
else output dat.claims;
```

We claim:

1. A method of underwriting group life insurance for a policy period comprising:

providing to a computer medical claims data for the group to be underwritten, each medical claim being related to a particular member of the group;

providing to a computer morbidity categories that can categorize medical claims, the morbidity categories relating diagnoses from medical claims that are generally homogeneous with respect to incidence of death;

categorizing with computer software configured to apply the morbidity categories data in the computer to each member's medical claims data in the medical claims data on the computer to generate on the computer each member's morbidity categories;

providing software configured to implement a death probability model for the likelihood of death arising from each morbidity category during the policy period derived from the formula:

probability (death occurring in the policy period given the morbidity category is present for the member)=probability (the morbidity category is present given all the death claims in a historical death claims or death certificate database)*probability (death in the policy period regardless of the morbidity category)/probability (morbidity category in medical claims);

applying the software configured to implement a death probability model to the member's morbidity categories for each member in the group on the computer to generate on the computer respective member's morbidity category probabilities of death occurring in the policy period for each member in the group;

calculating on the computer an expected death exposure for each member of the group in the member probability data on the computer from the probability of death occurring in the policy period for the member of the group;

summing on the computer the members' expected death exposures in the computer to form an expected group death exposure on the computer;

establishing an alternative price under the alternative pricing model;

calculating the ratio of the expected group disability exposure to the alternative pricing model's price;

setting a premium at a number between the alternative pricing model's price and the expected group disability exposure; and offering group life insurance coverage at the premium to the group.

2. The method of claim 1, further comprising adjusting the measure of the expected exposure using net present valuation methods.

3. The method of claim 1, wherein each medical claim has information about at least one medical condition, and information on the age and gender of each employee having medical claims in the group.

4. The method of claim 3, wherein the morbidity categories are age by gender strata by each medical condition, and the age by gender strata are used to define expected exposure.

5. The method of claim 1, wherein for each employee with multiple medical claims the expected conditional probability is adjusted for overlapping probabilities of death arising from the conditions indicated by the medical claims.

6. The method of claim 1 for situations where the offer is accepted by the group further comprising:

tracking the results;

modifying the premium to produce a desired loss ratio.

* * * * *